United States Patent [19]
Takimoto et al.

[11] Patent Number: 5,843,674
[45] Date of Patent: Dec. 1, 1998

[54] ANTI-HUMAN TYROSINASE MONOCLONAL ANTIBODY

[75] Inventors: Hiroyuki Takimoto; Satoshi Suzuki; Koushi Shibata; Shigeki Masui, all of Yokohama, Japan

[73] Assignee: Pola Chemical Industries Inc., Shizuoka, Japan

[21] Appl. No.: 504,048

[22] PCT Filed: Oct. 14, 1994

[86] PCT No.: PCT/JP94/01728

§ 371 Date: Jul. 14, 1995

§ 102(e) Date: Jul. 14, 1995

[87] PCT Pub. No.: WO95/14042

PCT Pub. Date: May 26, 1995

[30] Foreign Application Priority Data

Nov. 16, 1993 [JP] Japan ................................. 5-286861
Aug. 31, 1994 [JP] Japan ................................. 6-207123

[51] Int. Cl.⁶ .......................... A61K 39/395; C12N 5/12; G01N 33/53; G01N 33/573

[52] U.S. Cl. .......................... 435/7.1; 435/7.21; 435/7.23; 435/172.2; 435/331; 435/332; 435/338; 530/388.2; 530/388.26; 530/388.8; 530/388.85

[58] Field of Search .............................. 530/387.9, 388.1, 530/388.26, 388.2, 388.8, 388.85; 435/7.1, 7.21, 7.23, 172.2, 331, 332, 338, 388.2

[56] References Cited

PUBLICATIONS

Jimenez, J. Biol. Chem 266:1147–1156, 1991.
Kwon, Biochem Biophys Res Comm 153:1301–1309, 1988.
Bouchard, J. Exp. Med. 169:2029–2042, 1989.
Coump J. Inv. Dermatol 96:446–451, 1991.

M. McEwan et al., "Monoclonal Antibody against Human Tyrosinase and Reactive with Melanotic and Amelanotic Melanoma Cells", pp. 515–519, Journal of Investigative Dermatology, vol. 90, No. 4 (1988).

M. McEwan et al., "Monoclonal Antibody against a Melanosomal Protein in Melanotic and Amelanotic Human Melanoma Cells", pp. 1–7, Pigment Cell Research, vol. 2, No. 1 (1989).

B. Bouchard et al., "Production and Characterization of Antibodies against Human Tyrosinase", pp. 291–295, Journal of Investigative Dermatology, vol. 102, No. 3 (1994).

*Primary Examiner*—Toni R. Scheiner
*Assistant Examiner*—Nancy A. Johnson
*Attorney, Agent, or Firm*—Knobbe, Martens, Olson & Bear, LLP

[57] ABSTRACT

A mammal is immunized by using an antigen of a peptide having an amino acid sequence existing in a region having low homology to amino acid sequences of tyrosinase-related proteins but included in an amino acid sequence of human tyrosinase, and then the spleen cells of the mammal is fused with cultured cells to prepare a hybridoma producing monoclonal antibody which binds to human tyrosinase and mouse tyrosinase but does not bind to the tyrosinase-related proteins.

8 Claims, 8 Drawing Sheets

```
HUMAN            1         10        20        30        40        50        60
  TYROSINASE     M----LLAVLYC----LLWSPQTSAGHFPRAC--VCSKNL---MEKECCP---PWSG---
HUMAN TRP1         :   ::. : :    ::   :.   : : :.   :    :①:::    : ::
                 MSAPKLLS-LGCIFFPLLLFQQARAQFF-RQCATVEA--LRSGM---CCPDLSPVSGPGT
                           70        80        90        100       110       120
                 DRSPCGQLSGRGSCQNILL-SNAPLGPQFPFTGVDDRESWPSVFYNRTCQCSGNFMGFNC
                 ::  ::  ::::  :. .     :    :  : .::  :    :: ::  :.::::  :  ::: : ::
                 DR--CGSSSGRGRCEAVTADSR PHSPQTPHDGRRRREVWPLRFFNRTCHCNGNFSGHNC
                           130       140       150       160       170       180
                 GNCKFGFWGPNCTERRLLVRRNIFDLSAPEKDKFF-AY---L-T---L---AKHTISSDY
                 : :.   :.  : ::    :.. ::::. ::: ::..:  :       : :      : :.
                 GYCRPGYRGAACDERVLIVRRNLLDLSKEEKNHFVRALDMALRTTHPLFVIA--TRRSEE
                           190       200       210       220       230       240
                 VIPIGTYGQMKNGSTPMF-NDINIYDLFVWMHYY-VSMDALLG-G--S--EIWRDIDFAH
                 :  :. :     :       : :  :  : . :::  ::: :      : : :   : :.   :  :..:
                 -IL-GPDG---NY--PQFEN-ISITNTFVWTHYYSVKKTFL-GVGQESFGEV--D--FSH
                           250       260       270       280       290       300
                 EAPAFLPWHRLFLLRWE---QEIQKLTGDEN-FTIRYWDWRDAE-K--CDICTDEYMGGQ
                 :..::::.:::    ::: :    ::.   :     :  :..::..  :  :   ::::::. ::.
                 EGPAFLTWHRYHLLRLEKDMQEM--LQ--EPSFSLPYWNF--ATGKNVCDICTDDLMGSR
                           310       320       330       340       350       360
                 HPTNPNL-L-SPASFFSSWQIVC-SRLEEYNSHQSLCNGTPE-GPLRRNP-GNHDKSRTP
                    :  .   :  :: : :::   :  : .::   : ::.:..   .::: : :   ::.::::    :: ②:  :
                 S--NFDSTLISPNSVFSQWRVVCDS-LEDYDTLGTLCNST-EDGPIRRNPAGNVA--R-P
                           370       380       390       400       410       420
                 ---RLPSS-ADVEFCLS--L--TQYE-SGSMDKAANFSFRNTLEGFAS-PLTGIAD-ASQ
                    :::    .  : :.  ::       :   :        : :            :  :::::  ::   :  : ::.  : :
                 MVQRLPEPQAVVQ CLEVGLFDTPPFTSNST----N-SFRNTVEGT-SDP-TGLYDPAVR
                           430       440       450       460       470       480
                 SSMHNAL-HIYMNGT--NSQVQGSANDPIF-LLHHAFVDSIF-EQWLRRHR------PLQ
                 :  ::  :  :...:::  :. .   :.::::    :::    :  :..: : ::::          :  :
                 SL-HN-LAHLFLNGTGGNTHL--SPNDPIPVLLHT-FTDAVFDE-WLRRYNADISTFPL-
                           490       500       510       520       530       540
                 EVYPEANAPIGHNRESY-MVPFIPLYRNGDFFISSKD-LGYDYSYLQDSDPDS--FQDYI
                 :         :::::::::   : ::::  :   :   . :.. . :  :::  :       :③:  :    :
                 E-----NAPIGHNRQ-YNMVPFWPPVTNTQMFVTAPDNLGYTYEI-QW--P-SREF----
                           550       560       570       580       590       600
                 KSYLEQ-ASRIWSWLLGAAMVGAVLTALL-A---GLVSLLCRHKRKQLPEEKQPLLMEKE
                 :    :    :   :        : :::   :: ::    : :    :  : : :..: ④:   :::: ⑤
                 -SVPEIIA--I------AV-VGA-L--LLVALIFGTASYLIRARRSMD-EANQPLLT---
                           610
                 DYHSLYQSHL
                 :    ::
                 DQ---YQC--
```

FIG. 1

ANTI-HUMAN TYROSINASE MONOCLONAL ANTIBODY

TECHNICAL FIELD

The present invention relates to an anti-human tyrosinase monoclonal antibody, a method for producing the same, and a method for detecting human tyrosinase by using the monoclonal antibody.

BACKGROUND ART

Tyrosinase is the most important enzyme for in vivo biosynthesis of melanin pigment. It is acknowledged that tyrosinase is produced in ribosome of rough endoplasmic reticulum, then concentrated and activated in Golgi organ-related endoplasmic reticulum, and selectively transferred to premelanosome generated by Golgi organ.

Serious dermal disorders are known to occur when biosynthesis of tyrosinase is inhibited. For example, dyschromatosis is known to occur due to mutation of a structure of tyrosinase itself or due to abnormality in its biosynthesis process, while the selective transfer of tyrosinase to premelanosome has a possibility of contribution thereto. In recent years, increase in ozone holes results in increase in amount of ultraviolet light arriving at the surface of the earth. Associating increase in dermal cancers is worried worldwide. Among them, malignant melanoma is one type of dermal cancers, in which melanocyte cancerates while maintaining its function, especially tyrosinase productivity, which is known to have extremely strong malignancy, and metastasize to lymph node at a high frequency. If in an early stage, it can be cured by surgical excision over a wide region. In such a case, however, in order to decrease the load of a patient as small as possible, it is necessary to certainly remove lesions while minimizing the excision. However, no diagnostic agent which can completely judge the lesions has been known until present.

A knowledge of behavior of tyrosinase in a living body or cells has been believed to be extremely beneficial for diagnosis or elucidation of causes of such diseases. From such a viewpoint, efforts have been hitherto made to know behavior of tyrosinase. Especially, various investigations have been made for methods to use antigen-antibody reactions because of their high sensitivity, and polyclonal antibodies against tyrosinase have been prepared since the early days (for example, Jimenez, M. et al., (1991) *J. Biol. Chem.,* 266 (2), 1147–1156; Bouchard, B. et al., (1994) *J. Invest. Dermatol.,* 102 (3), 291–295).

However, polyclonal antibodies have a serious drawback in that the antibody titer largely disperses depending on lots, and the reproducibility is poor because they are prepared by immunizing an animal one by one and recovering them from its blood. Thus they are not practical, and have not been commercially produced. For this reason, trials have been made, in which an animal is immunized by using tyrosinase as an antibody, and then lymphocyte of the animal is fused with cultured cells such as myeloma to prepare hybridoma which is used to produce an anti-tyrosinase monoclonal antibody (Margherita Cuo-mo et al., *J. Invest. Dermatol.,* 96 (4), 446–451 (1991); Yasushi Tomita et al., *J. Invest. Dermatol.,* 85 (5), 426–430 (1985)).

However, it has been revealed afterward that those regarded as the anti-tyrosinase monoclonal antibody in the foregoing reports are monoclonal antibodies against tyrosinase-related proteins (Yasushi Tomita et al., *J. Invest. Dermato.,* 96 (4), 500–504 (1991)). This is due to the fact that the proteins called "tyrosinase-related proteins" (hereinafter referred to as "TRP") exist in a living body, as having extremely similar amino acid sequence and molecular weight to those of tyrosinase. Thus complete separation of tyrosinase from TRP is extremely difficult. Accordingly, contaminating TRP acts as an antigen, and an anti-TRP antibody is generated in the case of the conventional techniques in which an animal is immunized by using an antigen of tyrosinase purified from cells or tissues. Therefore, it is difficult to correctly detect tyrosinase by using such a monoclonal antibody.

McEwan et al. has reported an anti-human tyrosinase monoclonal antibody (McEwan, M. et al., *Pigment Cell Res.,* 2, 1–7 (1989)). However, a molecular weight (about 58 kd) of an antigen recognized by the monoclonal antibody is different from a molecular weight (about 75 kd) of human tyrosinase acknowledged by the present inventors. The monoclonal antibody of McEwan et al. weakly cross-reacts with mouse tyrosinase, however, its binding is weaker than that to human tyrosinase, and its epitope is also indefinite. Additionally, the staining factor was 0.1% when mouse melanoma cells were immunologically stained by using the anti-human tyrosinase monoclonal antibody of McEwan et al. Further, the anti-human tyrosinase monoclonal antibody was obtained by using the antigen of human tyrosinase itself purified from cultured cells. Thus a technique for isolating tyrosinase from a mixture containing contaminants difficult to be removed such as TRP is essential for preparation of cells which produce the monoclonal antibody. Accordingly, it is impossible to conveniently obtain the cells which produce the monoclonal antibody.

As described above, in order to elucidate causes of diseases resulting from abnormality of tyrosinase, it is believed to be extremely beneficial to know behavior of tyrosinase in a living body or cells. For such experiments or tests, however, it is preferable to use a laboratory animal. Thus a monoclonal antibody which binds to tyrosinase of an animal other than human is necessary. Accordingly, a monoclonal antibody has been desired, which binds to human tyrosinase and tyrosinase of an animal other than human, but does not binds to TRP.

DISCLOSURE OF THE INVENTION

The present invention has been made in accordance with the viewpoints described above, an object of which is to provide a monoclonal antibody which does not recognize TRP as an antigen but binds to human tyrosinase and tyrosinase of an animal other than human, and a method for detecting human tyrosinase by using the monoclonal antibody.

As a result of diligent studies by the present inventors to achieve the object described above, it has been found that a monoclonal antibody which does not bind to TRP but binds to human tyrosinase is obtained by using an antigen of a peptide having a sequence included in an amino acid sequence of human tyrosinase but having low homology to a sequence of TRP, and human tyrosinase can be specifically detected by using the same, arriving at completion of the present invention.

Namely, the present invention lies in a monoclonal antibody having the following properties:

(a) it binds to human tyrosinase;
(b) it binds to mouse tyrosinase; and
(c) it does not bind to tyrosinase-related proteins.

Further, the present invention lies in a method for producing the monoclonal antibody as defined above comprising the steps of:

(a) immunizing a mammal by using a conjugate of a carrier and a peptide having at least a part of an amino acid sequence existing in a region having low homology to amino acid sequences of tyrosinase-related proteins but included in an amino acid sequence of human tyrosinase, followed by excision of spleen cells of the mammal to be fused with cultured cells to prepare hybridoma;

(b) selecting a hybridoma which produces a monoclonal antibody which binds to human tyrosinase and mouse tyrosinase but does not bind to the tyrosinase-related proteins; and (c) collecting an antibody protein from a supernatant of a culture obtained by culturing the hybridoma in an appropriate medium or from an ascitic fluid obtained by culturing the hybridoma in an abdominal cavity of a mouse.

The present invention further provides a method for detecting human tyrosinase in accordance with an immunological method using a monoclonal antibody, wherein the aforementioned monoclonal antibody is used.

In this specification, the phrase "specifically binds to human tyrosinase" means that the monoclonal antibody binds to human tyrosinase but does not bind to the tyrosinase-related protein, however, the phrase does not means that the monoclonal antibody does not bind to mouse tyrosinase.

The present invention will be explained in detail below.

A cDNA sequence of human tyrosinase has been already known (Sigeki Shibahara et al., *Tohoku J. exp. Med.*, 156, 403–414 (1988)), and a cDNA sequence of human TRP has been also already known (Tirza Cohen et al., *Nucleic Acid Research*, Vol. 18, No. 9, 2807–2808 (1990)). The present inventors translated the cDNA sequences into amino acid sequences, and compared them (FIG. 1). In SEQ ID NO:8 and SEQ ID NO:9 and FIG. 1, an upper lane indicates the amino acid sequence of human tyrosinase (SEQ ID NO:8), and a lower lane indicates the amino acid sequence of TRP (SEQ ID NO:9) by using one letter symbols. A mark (:) indicated between the lanes represents a portion where amino acids are completely coincident, and a mark (.) represents a portion where amino acids are coincident in that they belong to an identical type of amino acids (hydrophobic, hydrophilic, basic and so on). As a result, it has been found that several portions having low homology to TRP are present in the amino acid sequence of human tyrosinase.

Taking notice of this point, the present inventors synthesized peptides having amino acid sequences of these portions (synthesis was entrusted to PEPTIDE Institute Inc.). Hybridoma were prepared by immunizing a mammal with five species of the obtained peptides, followed by excision of spleen cells which were fused with cultured cells. These hybridoma were allowed to produce monoclonal antibodies to search for a hybridoma which produced a monoclonal antibody which bound to human tyrosinase and mouse tyrosinase but did not bind to the tyrosinase-related proteins. As a result, the present inventors have succeeded in obtaining a hybridoma which produces a monoclonal antibody specific to tyrosinase from only one hybridoma prepared by using spleen cells of a mammal immunized with a synthesized peptide having a sequence shown in SEQ ID NO:1 (hereinafter also referred to as "peptide specific to human tyrosinase"). Further, the present inventors have succeeded in specifically detecting human tyrosinase by using the monoclonal antibody obtained as described above.

<1> Monoclonal Antibody used for the Invention

At first, the monoclonal antibody specific to human tyrosinase, and its production method will be explained in accordance with a procedure of production.

(1) Antigen

The peptide specific to human tyrosinase to be used for immunizing a mammal is exemplified by a peptide having a sequence shown in SEQ ID NO:1 or a partial sequence thereof. As shown in Examples described below, no strain which produces a monoclonal antibody which can detect human tyrosinase has been obtained from hybridoma prepared by using spleen cells of mammals immunized with peptides having sequences shown in SEQ ID NO:2 to NO:5. Thus it is speculated that a peptide having at least a part of the sequence shown in SEQ ID NO:1 is preferable as an antigen.

However, it cannot be denied that a monoclonal antibody which specifically recognizes human tyrosinase can be obtained even if another region having low homology to the amino acid sequence of the tyrosinase-related protein is used. The monoclonal antibody of the present invention includes a monoclonal antibody specific to human tyrosinase obtained by using a peptide having a sequence of such a region.

The peptide as described above can be partially obtained, for example, by isolation from a hydrolysate of tyrosinase, however, it is preferably chemically synthesized according to an ordinary method. For example, the aforementioned peptide can be obtained by inputting the aforementioned sequence using a commercially available peptide synthesizer. Alternatively, it may be obtained by entrusting to a company for practicing undertaken synthesis service for peptides.

The peptide thus obtained (hereinafter also referred to as "synthesized peptide") can be used as an antigen as it is, or can be used in conjugation with a carrier such as keyhole limpet hemocyanin (KLH), bovine serum albumin (BSA) and ovalbumin (OVA). Upon the use, such a carrier can enhance antigenicity if the peptide alone provides low antigenicity, or if it alone provides no antigenicity. In this case, an antibody against the carrier is produced, however, it can be removed in a step of selecting hybridoma.

(2) Immunization of Mammal

The mammal to be immunized with the antigen described above is not specifically limited, provided that it is a mammal usually used for immunological experiments, including, for example, mouse, rat and rabbit. A method for immunization may be conducted in accordance with an ordinary procedure for immunization. For example, a method is exemplified, in which a synthesized peptide or a synthesized peptide conjugated with a carrier is repeatedly administered several times in every one week or two weeks in a dosage of 0.5 mg/kg to 50 mg/kg together with Freund's complete adjuvant or incomplete adjuvant, and only the synthesized peptide is administered at least two weeks after the final administration to perform final immunization.

The amount of administration of the synthesized peptide or the synthesized peptide conjugated with the carrier in this case is appropriately about 0.5 mg/kg to 50 mg/kg per one dose. If the amount of administration is less than 0.5 mg/kg, the antibody is sometimes not sufficiently produced. If it exceeds 50 mg/kg, no further immunological effect can be expected, and there is a fear that immunological suppression may occur in vivo, and no aimed antibody may be obtained.

(3) Preparation of Hybridoma

The mammal immunized as described above is sacrificed three or four days after the final immunization, its spleen is excised, and spleen cells are obtained. The cells are fused with cultured cells as a fusion partner in the presence of a fusion accelerator, and a spleen cell-cultured cell hybridoma can be obtained by selecting obtained fused cells.

The cultured cells as the fusion partner are not specifically limited, provided that they are those which fuse with the spleen cell, for which myeloma cells are generally suitable. Those having a specified drug marker for selection are preferable in order to distinguish non-fused cells from fused cells after cell fusion.

There are exemplified those deficient in hypoxanthine guanine phosphoribosyltransferase. Such cells cannot grow in a medium added with hypoxanthine, aminopterin and thymidine (HAT medium). However, fused cells of such cells and normal cells can grow even in the HAT medium, which can be distinguished from non-fused cells. Concretely, there are exemplified commercially available strains of myeloma cells such as P3X63Ag8.653, P3/NSI/1-AG4-1, FO, and SP2/0/Ag14 strains. However, there is no limitation thereto.

Cell fusion is usually performed by mixing antibody-producing cells (spleen cells) with myeloma cells in a mixing ratio of 10:1 to 2:1 together with a fusion accelerator in a medium such as PRMI1640 and MEM. The fusion accelerator is not specifically limited, provided that it is a fusing agent usually used in cell fusion experiments. Concretely, there may be exemplified Sendai virus and polyethylene glycol having an average molecular weight of 500–7000. Alternatively, fusion may be performed by using electric pulse. Cells after completion of cell fusion are diluted, for example, with RPMI1640 or MEM medium. The cells washed by centrifugation are floated in a selection medium such as the HAT medium, and dispensed and poured into a multiplate or the like to perform cultivation. Thus only hybridoma are allowed to grow.

(4) Selection of Hybridoma

The hybridoma obtained as described above are a mixture of hybridoma which produce monoclonal antibodies against different antigenic determinant sites and a monoclonal antibody against a protein used as the carrier, as for peptides used as the antigen. Accordingly, a hybridoma is selected from them, which specifically binds to the aforementioned synthesized peptide, that is the peptide specific to human tyrosinase.

A preferable method for the selection is an enzyme-linked immunosorbent assay method (ELISA method) which uses the synthesized peptide used as the antigen. For example, the synthesized peptide is placed in a solid phase in a plastic plate, to which a supernatant of a culture of the hybridoma and an enzyme are added. The amount of antibody to bind to the synthesized peptide can be known according to the amount of binding of a fluorescent substance or a luminescent substance. Alternatively, the antibody produced by the hybridoma is placed in a solid phase, which may be sequentially incubated with the synthesized peptide and a secondary antibody labeled with an enzyme or the like.

Further, a hybridoma which produces a monoclonal antibody which binds to human tyrosinase and mouse tyrosinase but does not bind to the tyrosinase-related proteins is selected from the hybridoma which produce monoclonal antibodies which bind to the synthesized peptide.

One strain of the hybridoma obtained as described above has been deposited in National Institute of Bioscience and Human Technology of Agency of Industrial Science and Technology (1–3, Higashi 1-chome, Tsukuba-shi, Ibaraki-ken, Japan; zip code 305) since Oct. 28, 1993 as FERM P-13937, transferred from the original deposition to international deposition based on the Budapest Treaty on Oct. 6, 1994, and deposited under a deposition number of FERM BP-4824.

Another strain of the hybridoma obtained as described above has been deposited in National Institute of Bioscience and Human Technology of Agency of Industrial Science and Technology (1–3, Higashi 1-chome, Tsukuba-shi, Ibaraki-ken, Japan; zip code 305) since May 27, 1994 as FERM P-14340, transferred from the original deposition to international deposition based on the Budapest Treaty on Sep. 14, 1994, and deposited under a deposition number of FERM BP-4801.

(5) Preparation of Monoclonal Antibody Specifically Binding to Human Tyrosinase

In order to obtain a monoclonal antibody which specifically binds to human tyrosinase from the hybridoma obtained as described above, for example, a supernatant of a culture of the antibody-producing hybridoma cultured in an appropriate medium, or an ascitic fluid obtained by culturing the antibody-producing hybridoma in an abdominal cavity of a mouse is purified by ammonium sulfate fractionation, gel filtration, affinity chromatography and so on in accordance with an ordinary method. Thus the monoclonal antibody specific to human tyrosinase is obtained.

The anti-human tyrosinase monoclonal antibody of the present invention can be used for research for behavior of tyrosinase in a living body or cells. It can be also utilized for diagnosis or elucidation of causes of diseases relevant to tyrosinase, elucidation of pathology of dyschromatosis such as canities and albinism, and diagnostic agents used for detection of lesions, judgment of metastasis and the like of malignant melanoma. Further, the anti-human tyrosinase monoclonal antibody of the present invention binds to mouse tyrosinase. Thus the monoclonal antibody of the present invention can be utilized as a means for investigating behavior of the tyrosinase protein in animal tests for investigating behavior of the tyrosinase protein by using a colored mouse.

<2> Method for Detecting Human Tyrosinase of the Present Invention

The monoclonal antibody obtained as described above which specifically binds to human tyrosinase selectively binds to human tyrosinase. Thus human tyrosinase can be detected by application of a method for detecting antibodies using an ordinary antigen-antibody reaction. Human tyrosinase can be detected by using the monoclonal antibody of the present invention as an antibody for staining, for example, in immunological staining, Western blot (enzyme immunoblot), or microautoradiography of cultured cells, dermal tissues and the like originating from human. Additionally, the detection can be performed not only qualitatively but also quantitatively in accordance with a degree of staining or the like.

An exemplary method for detection by immunological tissue staining is as follows. Namely, a frozen section of human epidermal tissue or cultured cells originating from human is washed with PBS, then it is stained with the anti-human tyrosinase monoclonal antibody, it is washed again with PBS, and then the monoclonal antibody bound to the human tissue and the cultured cells is detected by using an FITC-labeled secondary antibody. Thus the human tyrosinase in the tissue of human and the cultured cells can be detected.

A method for detection by enzyme immunoblot is exemplified by the following method. For example, an extract of cultured pigment cells originating from human is separated by polyacrylamide gel electrophoresis, and then electrophoresed materials are transferred onto a nitrocellulose membrane or the like. Next, the membrane is washed with PBS or the like, and then a band of human tyrosinase on the membrane is stained with the anti-human tyrosinase monoclonal antibody. After washing with PBS or the like again, the stained band is detected with a commercially available enzyme-labeled secondary antibody, and the intensity of the band is measured. Thus the human tyrosinase can be detected quantitatively.

The method for detection of human tyrosinase of the present invention can be utilized for research for behavior of tyrosinase in a living body or cells, diagnosis or elucidation of causes of tyrosinase-related diseases, elucidation of pathology of dyschromatosis such as canities and albinism, and diagnosis such as detection of lesions and judgment of metastasis of malignant melanoma. The tyrosinase-related diseases include diseases caused by concernment of melanocyte, such as canities, freckles, flecks, chloasma, albinism, and senile melanoderma.

Further, it is expected that a substance for suppressing or facilitating melanin production can be screened by administrating samples to an animal, measuring tyrosinase protein in the animal in accordance with an immunological method using the monoclonal antibody of the present invention, and selecting a sample which causes variation of tyrosinase protein between its amounts before and after the administration.

BRIEF DESCRIPTION OF THE DRAWINGS

FIG. 1 shows homology in amino acid sequence between human tyrosinase and TRP, and positions of synthesized peptides on a human tyrosinase protein;

BEST MODE FOR CARRYING OUT THE INVENTION

Figure 2:
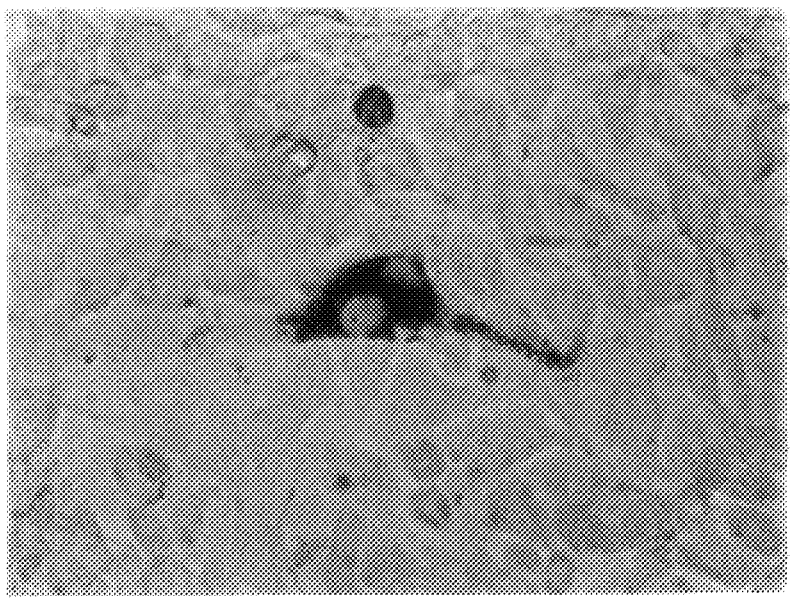
FIG. 2 is a photograph showing a result of investigation by a tyrosinase activity staining method for expression of a gene in human tyrosinase gene-introduced cells.

The present invention will be explained more concretely below with reference to Examples.

Example 1: Preparation of Monoclonal Antibody Specific to Human Tyrosinase

<1> Preparation of Hybridoma

Synthesis of peptides having amino acid sequences shown in SEQ ID NO:1 to NO:5 and conjugation with a carrier (KLH) were entrusted to PEPTIDE Institute Inc.

Five species of the carrier-conjugated synthesized peptide described above (100 μg) were dissolved in physiological saline (100 μl), and mixed and emulsified with complete Freund's adjuvant (produced by SIGMA) (100 μl), each of which was administered into an abdominal cavity of each of eight weeks-old BALB/c mice (CLEA Japan Inc.). After 1 week and 2 weeks, a mixed and emulsified solution (200 μl) containing equal amounts of each of the carrier-conjugated synthesized peptides described above and incomplete Freund's adjuvant was administered intraperitoneally. Two weeks after the third administration, a physiological saline (100 μl) prepared by dissolving 50 μg of the synthesized peptide was injected intravenously.

After 3 days, spleen was excised from each of the aforementioned mice. Spleen cells were suspended in an RPMI1640 medium, and washed. On the other hand, a mouse myeloma cell strain P3X63Ag8.653 (purchased from Dainippon Pharmaceutical Co., Ltd.) was cultured to arrive at its logarithmic growth phase in synchronization with cell fusion, and collected by centrifugation.

Myeloma cells ($2\times10^7$ cells) were mixed with the spleen cells ($10^8$ cells) in the medium described above, and the cells were pelleted by centrifugation. After removing a supernatant, an RPMI1640 medium (1 ml) containing 50% PEG 4000 (produced by SIGMA) at a temperature held at 37° C. was added dropwise over 1 minute, followed by gentle stirring for 1 minute. Further, the RPMI1640 medium at 37° C. (2 ml) was added dropwise over 2 minutes with stirring, followed by dropwise addition (8 ml) thereof over 3 minutes.

After completion of the dropwise addition, a supernatant was removed by centrifugation, and a cell pellet was suspended in 40 ml of a GIT medium (produced by Wako Pure Chemical Industries, Ltd.), which was dispensed and poured into 4 sheets of 96-well plates (produced by Sumitomo Bakelite Co., Ltd.) in an amount of 100 μl per one well. A HAT medium (25 μl) was added on the next day, and the HAT medium (25 μl) was further added after 4 days. After culturing for 1 week, a half of supernatant of the medium was removed, and a GIT medium (100 μl) was added.

Only hybridoma created by the fusion of the myeloma and spleen cells formed colonies about 2 weeks after the cell fusion, which were continuously cultured until the colonies had a diameter of about 1 mm. At this time point, antibodies secreted to supernatants of the cultures were assayed by a sandwich ELISA method by using the synthesized peptides described above and a commercially available secondary antibody (horseradish peroxidase (HRP) labeled goat anti-mouse Ig's (γ+L) antibody, produced by TAGO, Ltd.). Among them, hybridoma in wells having high antibody tires were cloned by a limiting dilution method, and monoclonal antibody-producing hybridoma strains were obtained.

Strains to produce monoclonal antibodies to bind to human tyrosinase were selected from the obtained hybridoma strains by an immunological staining method using human skin. As a result, a strain which produced a monoclonal antibody which bound to human tyrosinase was obtained only from hybridoma originating from the animal immunized by using the synthesized peptide having the amino acid sequence shown in SEQ ID NO:1.

One strain of the hybridoma obtained as described above (AHT-C2-H12) has been deposited in National Institute of Bioscience and Human Technology of Agency of Industrial Science and Technology (1–3, Higashi 1-chome, Tsukuba-shi, Ibaraki-ken, Japan; zip code 305) since Oct. 28, 1993 as FERM P-13937, transferred from the original deposition to international deposition based on the Budapest Treaty on Oct. 6, 1994, and deposited under a deposition number of FERM BP-4824. Another strain of the hybridoma obtained as described above (AHT-C2-H31) has been deposited in National Institute of Bioscience and Human Technology of Agency of Industrial Science and Technology (1–3, Higashi 1-chome, Tsukuba-shi, Ibaraki-ken, Japan; zip code 305) since May 27, 1994 as FERM P-14340, transferred from the original deposition to international deposition based on the Budapest Treaty on Sep. 14, 1994, and deposited under a deposition number of FERM BP-4801.

<2> Preparation of Monoclonal Antibody Specifically Binding to Human Tyrosinase (1) Preparation from Supernatant of Culture of Hybridoma Obtained in the Foregoing The hybridoma described above (FERM BP-4801) was cultured in 1 L of a GIT medium. A supernatant of the culture was recovered by centrifugation when the cell density reached $5 \times 10^6$ cells/ml, and it was filtrated by using a filter having a pore size of 0.22 mm. The filtrate was subjected to ammonium sulfate (50%) salt precipitation, and an obtained precipitate was recovered by centrifugation. The precipitate was dissolved in 2 ml of PBS, transferred to a dialysis tube (purchased from Sanko Junyaku Co., Ltd.), and then dialyzed in 2 L of PBS at 4° C. After completion of the dialysis, the solution was purified with a protein A column kit (produced by Amersham Japan). As a result, an anti-human tyrosinase monoclonal antibody solution in an amount of 3.5 mg (500 $\mu$g/ml×7 ml) was obtained from 1 L of the filtrate.

(2) Preparation from Mouse Ascitic Fluid

The hybridoma obtained in the foregoing (logarithmic growth phase) was inoculated in a culture flask at a cell density of $2 \times 10^5$ cells/ml one day before administration to a mouse, and cultured in a GIT medium. Cells were recovered by centrifugation after one day, and again suspended in a GIT medium at a cell density of $10^7$ cells/ml. The suspension was administered into an abdominal cavity in an amount of 1 ml for one eight weeks-old BALB/c nude mouse bred in an SPF region (purchased from CLEA Japan Inc.), and the mouse was continuously bred in the SPF region to allow the hybridoma to grow in the abdominal cavity. After 3 weeks, its abdomen had sufficient auxesis (with an approximate size of a pregnant mouse just before accouchement), and storage of ascitic fluid was recognized. Thus the ascitic fluid was recovered by using a syringe of 10 ml volume (produced by Terumo Corporation). The abdominal cavity was washed with about 3 ml of PBS per one mouse, and the washing solution was simultaneously recovered. The obtained ascitic fluid and washing solution were mixed (6 ml per one mouse), and filtrated with a filter having a pore size of 0.22 $\mu$l. An obtained filtrate was assigned to an anti-human tyrosinase monoclonal antibody-containing ascitic fluid (the anti-human tyrosinase monoclonal antibody-containing ascitic fluid is simply referred to as "monoclonal antibody-containing ascitic fluid" below). The obtained monoclonal antibody-containing ascitic fluid was purified with the protein A column kit described above. As a result, an anti-human tyrosinase monoclonal antibody solution at a concentration of about 1.2 mg/ml was obtained from 1 ml of the monoclonal antibody-containing ascitic fluid.

Example 2: Analysis and Evaluation of Anti-Human Tyrosinase Monoclonal Antibody

<1> Evaluation of Specificity of Anti-Human Tyrosinase Monoclonal Antibody

In order to evaluate the specificity of the monoclonal antibody obtained in the foregoing, human tyrosinase, mouse tyrosinase, human TRP-1 and human TRP-2 genes were introduced into mouse non-pigment-producing melanoma, namely K1735 cells (producing neither tyrosinase nor TRP-1; Yasushi Tomita et al., *J. Invest. Dermatol.*, 96 (4), 500–504 (1991); given from Medical Faculty of Tohoku University). Expressed cells were used to perform activity staining by the monoclonal antibody obtained in the foregoing.

(1) Preparation of Cells with Introduced Human Tyrosinase, Mouse Tyrosinase, Human TRP-1 and Human TRP-2

K1735 cells were inoculated in a petri dish for culturing having a diameter of 6 cm (produced by FALCON, Ltd.) with about $5 \times 10^5$ cells (about 75% confluent with respect to the petri dish), and cultured overnight in a DME medium (Dulbecco's Modified Eagle's Medium, purchased form SIGMA, Ltd.) containing 10% FBS. The medium was exchanged, and culturing was continued for further 2 hours. On the other hand, plasmids for expression of introducing genes (pRHOHT2, pRHOHTα and pCMVDTS; see below) were dissolved in a 100 times-diluted TE buffer (10 mM Tris, 1 mM EDTA, pH 7.5) at a concentration of 50 $\mu$g/ml to prepare plasmid solutions. 175.0 $\mu$l of a 2-fold concentration of HBS buffer (10 mM KCl, 10 mM D-glucose, 1.5 mM $Na_2HPO_4$, 50 mM HEPES, pH 7.1) and 22.05 $\mu$l of 2M $CaCl_2$ were mixed and cooled with ice, which were gradually added dropwise to 152.95 $\mu$l of the aforementioned plasmid solution previously cooled with ice to precipitate the plasmid. Cooling was continued with ice for further 10 minutes, followed by addition to the medium of K1735 cells described above to continue culturing (all solutions used herein were previously sterilized with a filter having a pore size of 0.22 mm). After 5 hours, the medium was removed, and the cells were washed once by using a TBS buffer (137 mM NaCl, 2.7 mM KCl, 25 mM Tris, pH 7.4). 5 ml of a TBS buffer containing 10% glycerol was added and left to stand for 5 minutes at room temperature. The solution was removed, and washing was again performed with a TBS buffer twice, followed by culturing in a DME medium containing 10% FBS. After 20 hours, in order to express the introduced genes, the cells were subjected to a heat shock treatment at 42° C. for 1 hour (the heat shock treatment was not performed in the case of introduction of pCMVDTS). Culturing was further performed for 16 hours to prepare gene-introduced cells.

The plasmids for expressing the genes used as described above were as follows. Namely, pRHOHT2 (Takeda, A. et al. *Biochem. Biophys. Res. Commun.*, 162, 984–990 (1989)) was used for expression of the human tyrosinase gene, pRHOHTα was used for expression of the human TRP1 gene, and pCMVDTS (Kouji Yokoyama et al., *Biochim. Biophis. Acta*, 1217, 317–321 (1994)) was used for expression of the human TRP2 gene, respectively. All of the plasmids for expression of the genes were given from Medical Faculty of Tohoku University.

(2) Confirmation of Expression of Human Tyrosinase and Mouse Tyrosinase Genes

In order to confirm expression of the human tyrosinase gene and the mouse tyrosinase gene in the human tyrosinase gene-introduced cells and the mouse tyrosinase gene-introduced cells prepared as described in (1), tyrosinase activity staining (DOPA staining) was performed by using the human tyrosinase gene-introduced cells and the mouse tyrosinase gene-introduced cells. A method is described below.

The gene-introduced cells were washed with PBS, then added with PBS containing 10% formalin, and cooled with ice for 30 minutes. The cells were immersed three times in PBS at pH 6.8 for 10 minutes, added with PBS at pH 6.8 containing 0.1% L-DOPA, and reacted at 37° C. for 3 hours. After completion of the reaction, the cells were washed three times with PBS, again added with PBS containing 10% formalin, incubated at room temperature for 30 minutes, and then observed under a microscope. A result is shown in FIG. 2.

As understood from this figure, the cells with introduced human tyrosinase gene were stained black by the activity staining (the cells with introduced mouse tyrosinase gene were also stained black by the activity staining (photograph is not shown)). On the other hand, cells with no introduced gene were not stained. Namely, it was clarified that the cells with introduced human tyrosinase and mouse tyrosinase genes expressed the human tyrosinase and mouse tyrosinase genes.

(3) Reactivity of Anti-Human Tyrosinase Monoclonal Antibody with Human Tyrosinase and Mouse Tyrosinase Reactivity of the anti-human tyrosinase monoclonal antibody with human tyrosinase and mouse tyrosinase was investigated by immunological staining by using the human tyrosinase gene-introduced cells and the mouse tyrosinase gene-introduced cells with their expression having been confirmed in (2). A method is shown below.

Figure 3:
FIG. 3 is a photograph showing a result of immunological staining of human tyrosinase gene-introduced cells with an anti-human tyrosinase monoclonal antibody.
Figure 4:
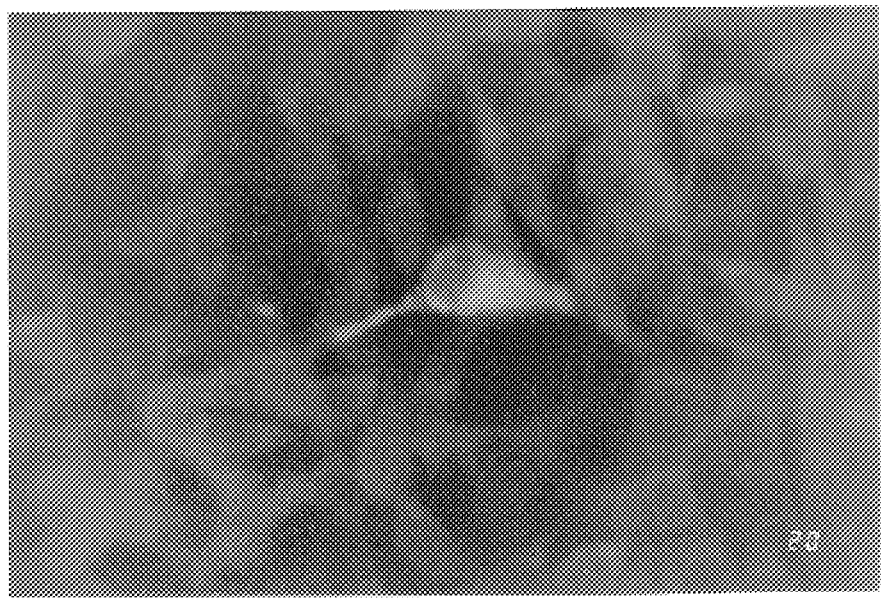
FIG. 4 is a photograph showing a result of immunological staining of mouse tyrosinase gene-introduced cells with an anti-human tyrosinase monoclonal antibody.
Figure 5:
FIG. 5 is a photograph showing a result of immunological staining of cells having no introduced gene with an anti-human tyrosinase monoclonal antibody.

After removing the medium from the cells in culture with the introduced human tyrosinase and mouse tyrosinase genes obtained in the foregoing, the cells were added with PBS containing 10% formalin, and treated at room temperature for 20 minutes. After washing with PBS three times, the cells were further added with PBS containing 0.5% Triton X-100, treated at room temperature for 5 minutes, and washed with PBS once. Next, the aforementioned anti-human tyrosinase monoclonal antibody solution (either the antibody solution prepared from the culture supernatant or the antibody solution prepared from the antibody-containing ascitic fluid) diluted to a concentration of 10 $\mu$g/ml with PBS was added dropwise to the cell surfaces as a primary antibody, followed by incubation at 37° C. for 30 minutes. After washing with PBS three times again, commercially available biotin-conjugated anti-mouse IgG (produced by CHEMICON, Ltd.) diluted 50 times with PBS was added dropwise to the cell surfaces as a secondary antibody. The cells were treated at 37° C. for 30 minutes, and washed with PBS three times. Next, commercially available FITC-conjugated avidin (produced by BIOMEDA, Ltd.) diluted 100 times with PBS was added. The cells were incubated at 37° C. for 30 minutes, and washed three times with PBS. Finally, the cells were enclosed by adding 50% glycerol-containing PBS and quietly placing a cover glass, and then observed and photographed under a fluorescence microscope (BH2-RFCA, produced by Olympus Optical Co., Ltd.). Results are shown in FIGS. 3, 4 and 5.

As understood from these figures, the cells with the introduced human tyrosinase gene and the mouse tyrosinase gene were intensively stained by the anti-human tyrosinase monoclonal antibody. Namely, it has been clarified that the monoclonal antibody of the invention binds not only to human tyrosinase but also to mouse tyrosinase. Therefore, the monoclonal antibody of the invention can be utilized in tests using not only human but also mouse (laboratory animal). On the other hand, cells with no introduced gene were not stained at all. Thus it has been found that the monoclonal antibody of the invention does not react with the original K1735 cells.

Further, the staining character was compared between cultured cells (melanoma cells) originating from mouse and human. Thus the reactivity of the antibody of the invention was compared between human tyrosinase and mouse tyrosinase.

MeWo, HMVII (RCB777: RIKEN Tsukuba Cell Bank, Japan) and G361 (ATCC CRL1424) were used as melanoma cells originating from human. B16 (ATCC CRL6233) and S91 (ATCC CLL 53.1) were used as melanoma cells originating from mouse. Each of them was cultured in each of petri dishes, a supernatant of the culture was removed, and the cells were washed several times with PBS. A blocking solution (PBS containing 5% FBS and 1% BSA) was poured into each petri dish to perform incubation at room temperature for 20 minutes. Further, the petri dishes were placed in a moisturized box, and the aforementioned monoclonal antibody solution diluted to 10 $\mu$g/ml with the blocking solution was added to the petri dishes to perform incubation at room temperature. After 1 hour, the petri dishes were washed for 5 minutes with PBS three times. A commercially available biotin-conjugated anti-mouse IgG goat antibody (produced by Chemicon, Ltd.) solution diluted 50 times with the blocking solution was poured into the petri dishes to perform incubation at room temperature. After 1 hour, the petri dishes were washed with PBS as described above, an FITC-conjugated avidin (produced by BIOMEDA, Ltd.) solution diluted 100 times with the blocking solution was poured to perform incubation at a dark place at room temperature for 1 hour. The petri dishes were again washed with PBS as described above, plate surfaces were coated with PBS containing 50% glycerol before drying of the petri dishes, and cover glasses were placed. Each of the petri dishes was observed by using a fluorescence microscope (BH2-RFCA, produced by Olympus Optical Co., Ltd.), and the ratio of stained cells was investigated. Results are shown in Table 1.

TABLE 1

| Cell species (melanoma) | Ratio of stained cells (%) |
|---|---|
| from human | |
| MeWo | 98 |
| HMVII | 95 |
| G361 | 97 |
| from mouse | |
| B16 | 96 |
| S91 | 96 |

According to the results, it is understood that the antibody of the invention has the equivalent reactivity to human tyrosinase and mouse tyrosinase.

(4) Confirmation of Expression of Human TRP-1 Gene

Figure 6:
FIG. 6 is a photograph showing a result of investigation by immunological staining using an anti-TRP-1 antibody for expression of a gene in human TRP-1 gene-introduced cells.

In order to examine whether or not the human TRP-1 gene was expressed in the cells with introduced human TRP-1 gene prepared as described in (1), immunological staining of the cells with introduced human TRP-1 was performed by using an anti-TRP-1 antibody (given from Medical Faculty of Akita University). The immunological staining was performed in accordance with a method approximately the same as that described in (3). However, the aforementioned anti-human TRP-1 antibody was used as a primary antibody, and a commercially available texas red-conjugated anti-rat IgG goat antibody (produced by CALTAG, Ltd.) diluted 50 times with PBS was used as a secondary antibody. Further, the FITC-conjugated avidin treatment and the following operation of washing with PBS were omitted. A result is shown in FIG. 6.

As understood from the figure, the cells with introduced human TRP-1 gene were stained with the anti-TRP-1 antibody. On the other hand, cells without introduced gene were not stained with the anti-TRP-1 antibody (photograph is not shown). According to this fact, it was clarified that the cells with introduced human TRP-1 gene expressed human TRP-1.

(5) Reactivity Between Anti-Human Tyrosinase Monoclonal Antibody and Human TRP-1

Figure 7:
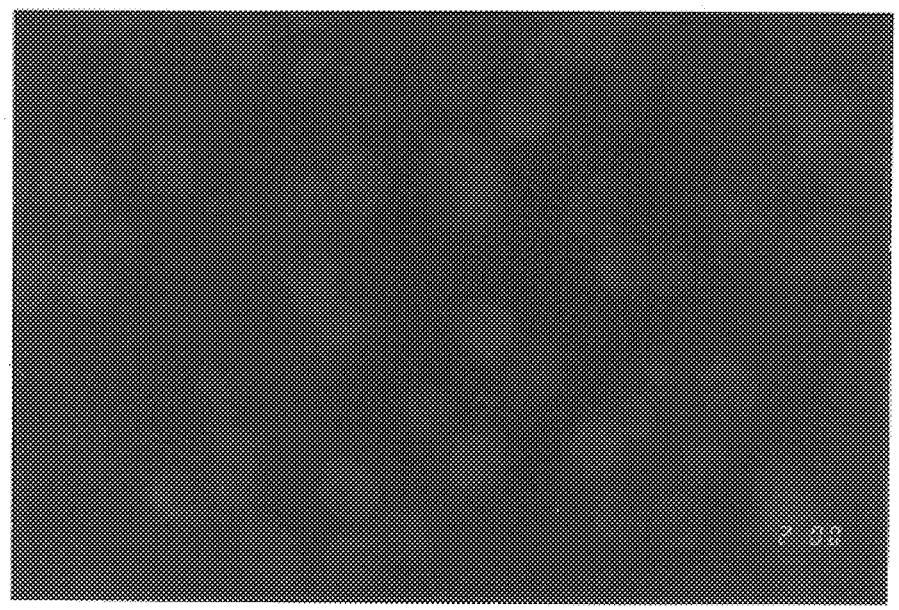
FIG. 7 is a photograph showing a result of immunological staining of human TRP-1 gene-introduced cells with an anti-human tyrosinase monoclonal antibody.

The reactivity between the anti-human tyrosinase monoclonal antibody and the human TRP-1 was investigated by immunological staining by using the cells with introduced human TRP-1 gene with the expression of the gene confirmed in (4). The immunological staining was performed in accordance with the method described in (3). A result is shown in FIG. 7.

As understood from the figure, the anti-human tyrosinase monoclonal antibody did not stain the cells with introduced human TRP-1 gene at all. Thus it was clarified that the monoclonal antibody of the invention did not react with human TRP-1.

(6) Confirmation of Expression of Human TRP-2 Gene

Figure 8:
FIG. 8 is a photograph showing a result of investigation by immunological staining using an anti-human TRP-2 antibody for expression of human TRP-2 in human TRP-2- gene introduced cells.

In order to examine whether or not the human TRP-2 was expressed in the cells with introduced human TRP-2 gene prepared as described in (1), immunological staining of the cells with introduced human TRP-2 gene was performed by using an anti-TRP-2 antibody (given from Medical Faculty of Tohoku University). The immunological staining was performed in accordance with a method approximately the same as that described in (3). However, the aforementioned anti-TRP-2 antibody diluted 100 times with PBS was used as a primary antibody, and a commercially available biotin-conjugated anti-rabbit IgG goat antibody (produced by TAGO, Ltd.) diluted 50 times with PBS was used as a secondary antibody. A result is shown in FIG. 8.

As understood from the figure, the cells with introduced human TRP-2 gene were stained with the anti-human TRP-2 antibody. On the other hand, cells without introduced gene were not stained with the anti-human TRP-2 antibody (photograph is not shown). According to this fact, it was clarified that the cells with introduced human TRP-2 expressed human TRP-2 gene.

(7) Reactivity Between Anti-Human Tyrosinase Monoclonal Antibody and Human TRP-2

Figure 9:
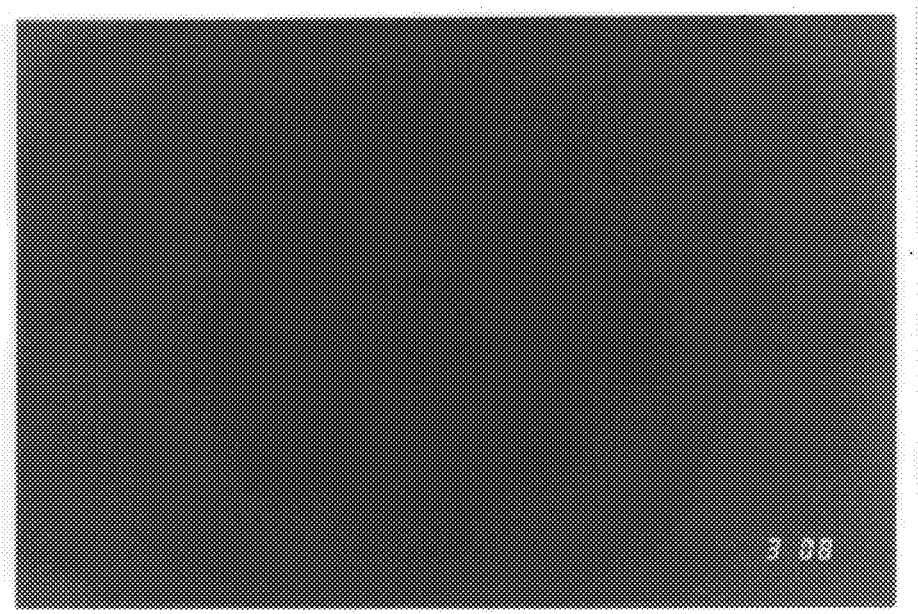
FIG. 9 is a photograph showing a result of immunological staining of human TRP-2 gene-introduced cells with an anti-human tyrosinase monoclonal antibody.

The reactivity between the anti-human tyrosinase monoclonal antibody and the human TRP-2 was investigated by immunological staining by using the cells with introduced human TRP-2 gene with the expression of the gene confirmed in (6). The immunological staining was performed in accordance with the method described in (3). A result is shown in FIG. 9.

As understood from the figure, the anti-human tyrosinase monoclonal antibody did not stain the cells with introduced human TRP-2 gene at all. Thus it was clarified that the monoclonal antibody of the invention did not react with human TRP-2.

Namely, it has been found that the monoclonal antibody obtained in the foregoing is an antibody completely different from the anti-tyrosinase monoclonal antibody (anti-TRP-1 antibody) in the prior art, and does not bind to TRP-1 as well as TRP-2.

<2> Isotype of Anti-Human Tyrosinase Monoclonal Antibody

The isotype of the monoclonal antibody obtained in the foregoing was investigated by using an isotyping kit (produced by Amersham Japan). As a result, it was immunoglobulin G1 (IgG1), and its L-chain was kappa (κ).

<3> Analysis of Epitope of Anti-Human Tyrosinase Monoclonal Antibody

The epitope of the anti-human tyrosinase monoclonal antibody obtained in Example 1 was investigated by using an epitope determining kit (SPOTs kit, produced by Funakoshi, Ltd.). As a result, it was found that the epitope of the antibody of the invention was Glu Asp Tyr His (SEQ ID NO:6), and especially Asp Tyr His was essential for recognition by the antibody of the invention. The epitope is completely coincident with a sequence contained in human tyrosinase (corresponding to amino acid numbers 4–7 in SEQ ID NO:1).

On the other hand, a sequence Asp Asp Tyr His (SEQ ID NO:7) is present at a carboxy terminal in an amino acid sequence of mouse tyrosinase. It can be understood well that the antibody of the invention can recognize this sequence as an epitope because Glu and Asp are extremely similar amino acids both having a carboxyl group at their side chains.

Example 3: Detection of Human Tyrosinase (I)

Evaluation of specificity was made for the monoclonal antibody obtained in Example 1 in accordance with an enzyme immunoblot method by using extracts of MeWo cells (cultured cells originating from human malignant melanoma) and HeLa cells (cultured cells originating from human uterocervical cancer). The method is explained in detail below.

Culture supernatants of the MeWo and Hela cells cultured in culturing flasks were removed, and the cells were recovered by using a rubber policeman after washing with PBS several times. The recovered cells were washed again with PBS several times, and suspended in suspensions for cell lysis (0.1M sodium phosphate buffer containing 0.5% Triton X-100, pH 8.9).

The cells were ground with a ultrasonic cell grinder (produced by TOSO Electronic Inc.), and centrifuged at 16,000 G for 10 minutes. The concentrations of protein contained in obtained supernatants were measured, and cell extract solutions were prepared. These were subjected to polyacrylamide gel (PAGEL, produced by ATTO, Ltd.) electrophoresis with density gradient of 5–20% at 4° C. (amount of application was 20 μg in protein amount per 1 lane). The electrophoresis was performed in accordance with an ordinary method. After completion of the electrophoresis, the gel was taken out, and immersed in a transfer buffer (100 mM Tris, 192 mM glycine). By using a blotting apparatus (semidry blotting apparatus, produced by ATTO, Ltd.), electrophoresed materials were transferred at 4° C. for 16 hours to a membrane (Immobilon, produced by Millipore Ltd.) previously immersed in the transfer buffer (the current during transfer was 0.25 mA per 1 cm$^2$ of the membrane).

A part of the membrane containing transferred electrophoresed materials (portion corresponding to 1 lane during the electrophoresis) was cut, washed with a 0.3M phosphate buffer (pH 6.6) for 5 minutes twice, and then reacted in a 0.1M phosphate buffer (pH 6.8) containing 0.1% L-DOPA at 37° C. for 3 hours. Thus the activity staining (DOPA staining) of human tyrosinase was performed, and the position of human tyrosinase on the membrane was detected.

On the other hand, the remainder of the membrane was immersed in a TBS buffer (20 mM Tris, 500 mM NaCl, pH 7.5) for 15 minutes, then immersed in a blocking buffer (5% skim milk or 1% BSA, and 0.1% Tween 20/TBS buffer), and stirred gently at room temperature for 1 hour.

After that, the membrane was washed with the 0.1% Tween 20/TBS buffer (TTBS buffer) (for 15 minutes once and for 5 minutes twice), immersed in a diluted solution of the monoclonal antibody obtained in Example of production (about 2 ml of a solution obtained by dilution to 2.5 $\mu$g/ml with the TTBS buffer), and stirred gently at room temperature for about 1 hour. The membrane was washed with the TTBS buffer as described above, immersed in a solution of a commercially available secondary antibody (about 2 ml obtained by dilution of 15,000 times using horseradish peroxidase (HRP) labeled anti-mouse Ig's ($\gamma$+L) goat antibody, produced by TAGO, Ltd.), and stirred gently at room temperature for about 1 hour.

The membrane was washed with the TTBS buffer (for 15 minutes once and for 5 minutes four times), and then a band of the electrophoresed materials to which the anti-human tyrosinase monoclonal antibody bound was detected by using a commercially available HRP detection kit (ECL kit, produced by Amersham, Ltd.). Alternatively, the band to which HRP binds can be also detected by using 4-chloro-1-naphthol as a substrate.

Figure 10:
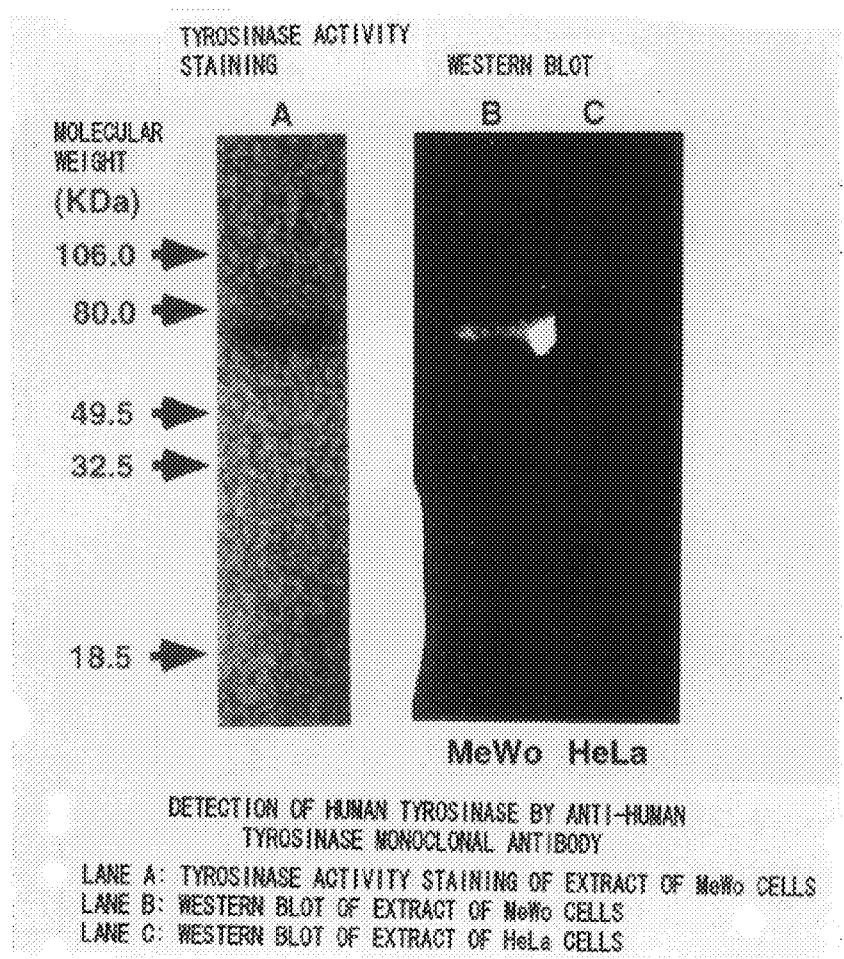
FIG. 10 is photographs showing results of electrophoresis in accordance with activity staining and enzyme immunoblot of tyrosinase.

A result of the aforementioned activity staining and a result of the enzyme immunoblot are shown in FIG. 10. As clarified from these results, the monoclonal antibody obtained in the foregoing binds to the band of protein having the human tyrosinase activity. Namely, it binds to human tyrosinase. Further, the monoclonal antibody does not bind to the extract from HeLa cells. Therefore, it is clear that human tyrosinase can be detected according to the present invention.

Example 4: Detection of Human Tyrosinase (II)

Immunological staining for a human epidermal tissue was performed by using the monoclonal antibody obtained in Example 1. Details are shown below.

Figure 11:
FIG. 11 is a photograph showing human skin subjected to immunological tissue staining by using an anti-human tyrosinase monoclonal antibody.

A human epidermal tissue (given from Medical Faculty of Tohoku University) previously frozen at −80° C. was embedded by using an embedding agent (Tissue-Tek O.C.T. Compound, produced by MILES Inc.). A frozen tissue section (5 mm of one side) having a thickness of about 5–10 mm was prepared by using an apparatus for preparing frozen sections (Cryostat, produced by BRIGHT Instrument company Ltd.), and then placed on a slide glass coated with 1% gelatin (slide glass with placed human epidermal tissue section is hereinafter simply referred to as "slide glass"). The slide glass was incubated at 37° C. for 1 hour, and then immersed in PBS once. Next, a blocking solution (PBS containing 5% FBS and 1% BSA) was added dropwise onto the tissue section to perform incubation at room temperature for 20 minutes. The slide glass was placed in a moisturized box, and the aforementioned monoclonal antibody diluted to 10 $\mu$g/ml with the blocking solution was added dropwise onto the tissue section to perform incubation at room temperature. After 1 hour, the slide glass was taken out from the moisturized box, and washed with PBS for 5 minutes three times. The slide glass was again placed in a moisturized box, and a commercially available biotin-conjugated anti-mouse IgG goat antibody (produced by Chemicon, Ltd.) diluted 50 times with the blocking solution was added dropwise onto the section to perform incubation at room temperature. After 1 hour, the slide glass was washed with PBS as described above, and placed in a moisturized box. An FITC-conjugated avidin (produced by BIOMEDA, Ltd.) diluted 100 times with the blocking solution was added dropwise onto the tissue section to perform incubation at a dark place at room temperature for 1 hour. The slide glass was taken out again, and washed with PBS as described above. Before drying of the tissue section, PBS containing 50% glycerol was added dropwise onto the tissue section, and a cover glass was placed thereon to perform observation and photographing by using a fluorescence microscope (BH2-RFCA, produced by Olympus Optical Co., Ltd.). A result is shown in FIG. 11.

According to the result, it is understood that in the human tissue, melanocyte with matured type tyrosinase present therein was intensively stained, while keratinocyte in epidermis and fibroblast in dermis were not stained at all. According to the foregoing, it is clear that the anti-human tyrosinase monoclonal antibody has excellent specificity to human tyrosinase, and human tyrosinase can be detected by using it.

Example 5: Detection of Human Tyrosinase (III)—
Immunological Staining of Metastasized Lesion of
Malignant Melanoma Immunological staining of a lesion of malignant melanoma metastasized to human lymph node was performed by using the monoclonal antibody obtained in Example 1. Details are shown below.

Figure 13:
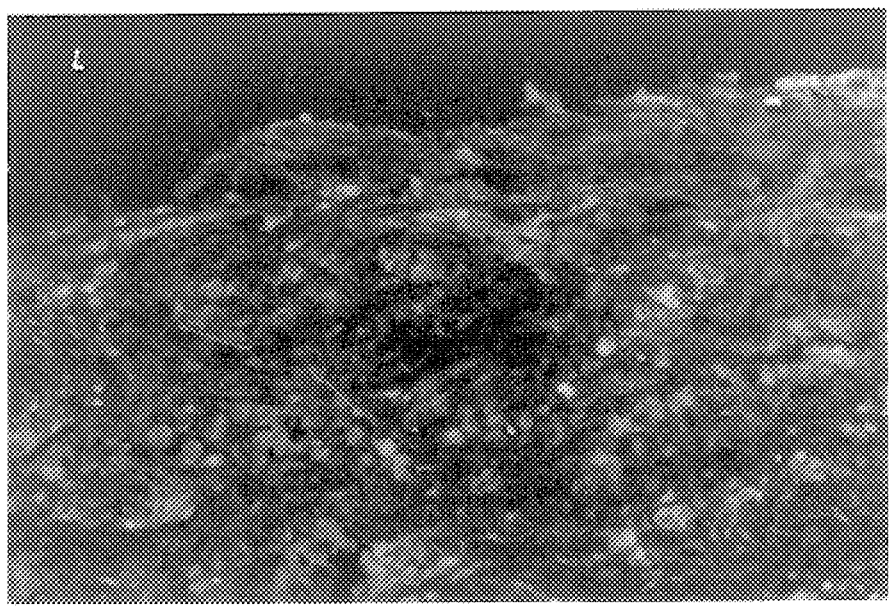
FIG. 13 is a photograph showing a result of immunological staining of a metastasized lesion of malignant melanoma of human lymph node by using an anti-human tyrosinase monoclonal antibody.
Figure 14:
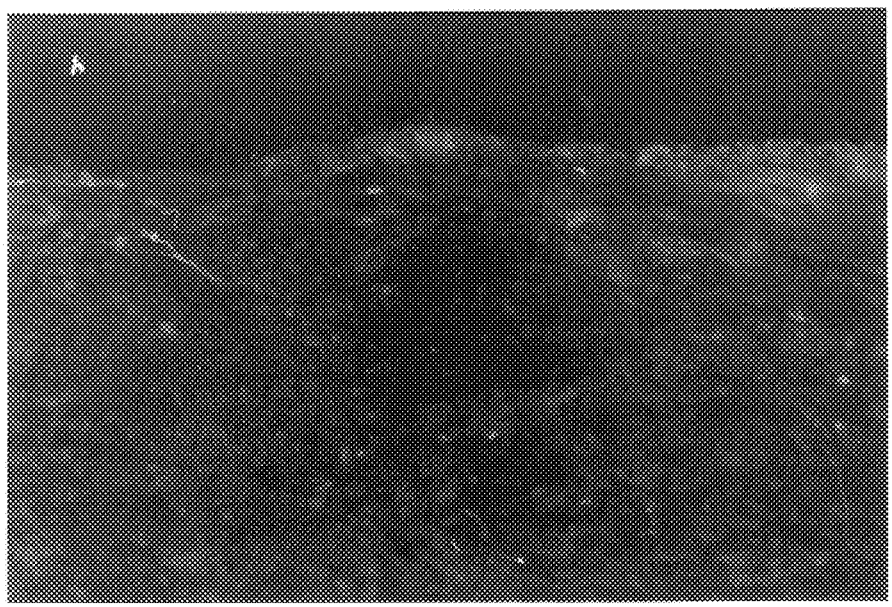
FIG. 14 is a photograph showing a result of immunological staining of a metastasized lesion of malignant melanoma of human lymph node without using an anti-human tyrosinase monoclonal antibody.

A frozen tissue or a paraffin-embedded tissue of human lymph node with metastasized malignant melanoma was stained with the anti-human tyrosinase monoclonal antibody in accordance with the method described in Example 4. A tissue not treated with the anti-human tyrosinase monoclonal antibody was used as a control. In order to confirm metastasis of malignant melanoma to lymph node, the DOPA staining of the tissue was performed in accordance with the method shown in Example 1. Results are shown in FIGS. 12, 13 and 14.

Figure 12:
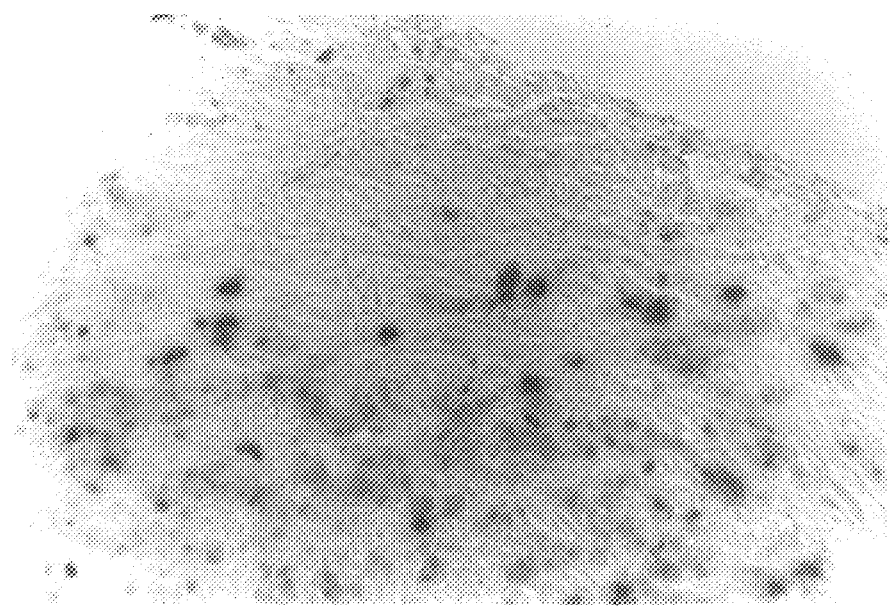
FIG. 12 is a photograph showing a result of investigation by activity staining of tyrosinase for metastasis of malignant melanoma to lymph node of human.

It is understood from FIG. 12 that the lymph node tissue was stained by the DOPA staining, and malignant melanoma certainly metastasized to the lymph node used. On the other hand, according to FIGS. 13 and 14, the tissue not treated with the anti-human tyrosinase monoclonal antibody was not stained at all, while the tissue treated with the anti-human tyrosinase monoclonal antibody was stained by the DOPA staining with high sensitivity. Accordingly, the anti-human tyrosinase monoclonal antibody can detects tyrosinase which is absent in a normal lymph node, but present only in the lymph node with metastasized malignant melanoma. Namely, it is clear that the anti-human tyrosinase monoclonal antibody can be used as a diagnostic agent for judging metastasis of malignant melanoma to human lymph node. Besides, staining can be also conducted in a primary lesion of malignant melanoma, and its stained image is completely different from that of skin of a healthy person. Thus the anti-human tyrosinase monoclonal antibody can be also used as a diagnostic agent for determining a range of excision of malignant melanoma. Further, a sample of such a lesion may be paraffin-embedded. Thus the anti-human tyrosinase monoclonal antibody can be used in general clinical situations.

Industrial Applicability

The present invention uses the monoclonal antibody having excellent specificity to human tyrosinase. Thus human tyrosinase can be specifically detected. Further, the antibody of the invention also binds to mouse tyrosinase. Thus tyrosinase of laboratory animals can be also detected. Furthermore, the antibody of the invention can be used for elucidation of pathology of dyschromatosis such as canities and albinism, or diagnosis of primary and metastasized lesions of malignant melanoma.

What is claimed is:

1. A monoclonal antibody having the following properties:
   (a) it specifically binds to human tyrosinase and mouse tyrosinase, wherein said monoclonal antibody specifically binds to a peptide having a sequence within the sequence of SEQ ID NO:1 and including the amino acid sequence Asp Tyr His;
   (b) it does not specifically bind to tyrosinase-related proteins; and
   (c) it recognizes an epitope of Glu Asp Tyr His (SEQ ID NO:6);
   said monoclonal antibody being obtained by a method comprising the steps of:
   (i) immunizing a mammal by using a conjugate of a carrier and a peptide having the amino acid sequence listed as SEQ ID NO:1, followed by excision of spleen cells of the mammal to be fused with cultured cells, thereby preparing hybridomas;
   (ii) selecting a hybridoma among said hybridomas prepared in step (i) which produces a monoclonal antibody which specifically binds to human tyrosinase and mouse tyrosinase but does not specifically bind to tyrosinase-related proteins; and
   (iii) collecting an antibody protein from a supernatant of a culture obtained by culturing said hybridoma selected in step (ii) in an appropriate medium or from an ascitic fluid obtained by culturing said hybridoma in the abdominal cavity of a mouse.

2. A monoclonal antibody according to claim 1, wherein its isotype is IgG1.

3. A method for producing the monoclonal antibody as defined in claim 1 comprising the steps of:

(a) immunizing a mammal by using a conjugate of a carrier and a peptide having the amino acid sequence listed as SEQ ID NO:1, followed by excision of spleen cells of the mammal to be fused with cultured cells to prepare hybridomas;
   (b) selecting a hybridoma among said hybridomas prepared in step (a) which produces said monoclonal antibody; and
   (c) collecting said antibody from a supernatant of a culture obtained by culturing said hybridoma selected in step (b) in an appropriate medium or from an ascitic fluid obtained by culturing said hybridoma in the abdominal cavity of a mouse.

4. A method for detecting human tyrosinase in accordance with an immunological method using a monoclonal antibody, wherein the monoclonal antibody as defined in claim 1 is used.

5. A method for diagnosing pigment-related diseases, wherein human tyrosinase is detected in accordance with the method as defined in claim 4.

6. A diagnostic agent for malignant melanoma containing the monoclonal antibody as defined in claim 1 as an active ingredient.

7. A method for detecting malignant melanoma of animals wherein tyrosinase is detected in accordance with an immunological method using the monoclonal antibody as defined in claim 1.

8. Monoclonal antibody produced by the hybridoma deposited with the National Institute of Bioscience and Human Technology of the Agency of Industrial Science and Technology (Japan) under Accession No. FERM BP-4801.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Met  Glu  Lys  Glu  Asp  Tyr  His  Ser  Leu  Tyr  Gln  Ser  His  Leu
 1              5                        10
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
His  Phe  Pro  Arg  Ala  Cys  Val  Ser  Ser  Lys  Asn  Leu  Met  Glu  Lys  Glu
 1              5                        10                       15
Cys
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

Pro Glu Gly Pro Leu Arg Arg Asn Pro Gly Asn His Asp Lys Ser Arg
 1               5                   1 0                  1 5

Thr Pro Arg ( 2 ) INFORMATION FOR SEQ ID NO:4:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:4:

Ile Ser Ser Lys Asp Leu Gly Tyr Asp Tyr Ser Tyr Leu Gln Asp Ser
 1               5                   1 0                  1 5

Asp Pro Asp ( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:5:

Val Leu Thr Ala Leu Leu Ala Gly Leu Val Ser Leu Leu Cys Arg His
 1               5                   1 0                  1 5

Lys Arg Lys Gln Leu Pro Glu Glu Lys
                2 0                  2 5

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vi) ORIGINAL SOURCE:

(xi) SEQUENCE DESCRIPTION: SEQ ID NO:6:

Glu Asp Tyr His
1

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

Asp Asp Tyr His
1

(2) INFORMATION FOR SEQ ID NO:8:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

Met Leu Leu Ala Val Leu Tyr Cys Leu Leu Trp Ser Pro Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
        130                 135                 140

```
Ile  Ser  Ser  Asp  Tyr  Val  Ile  Pro  Ile  Gly  Thr  Tyr  Gly  Gln  Met  Lys
145                 150                      155                           160

Asn  Gly  Ser  Thr  Pro  Met  Phe  Asn  Asp  Ile  Asn  Ile  Tyr  Asp  Leu  Phe
               165                      170                      175

Val  Trp  Met  His  Tyr  Tyr  Val  Ser  Met  Asp  Ala  Leu  Leu  Gly  Gly  Ser
              180                      185                           190

Glu  Ile  Trp  Arg  Asp  Ile  Asp  Phe  Ala  His  Glu  Ala  Pro  Ala  Phe  Leu
          195                      200                      205

Pro  Trp  His  Arg  Leu  Phe  Leu  Leu  Arg  Trp  Glu  Gln  Glu  Ile  Gln  Lys
     210                      215                      220

Leu  Thr  Gly  Asp  Glu  Asn  Phe  Thr  Ile  Arg  Tyr  Trp  Asp  Trp  Arg  Asp
225                      230                      235                           240

Ala  Glu  Lys  Cys  Asp  Ile  Cys  Thr  Asp  Glu  Tyr  Met  Gly  Gly  Gln  His
                245                      250                                255

Pro  Thr  Asn  Pro  Asn  Leu  Leu  Ser  Pro  Ala  Ser  Phe  Phe  Ser  Ser  Trp
               260                      265                      270

Gln  Ile  Val  Cys  Ser  Arg  Leu  Glu  Glu  Tyr  Asn  Ser  His  Gln  Ser  Leu
          275                      280                      285

Cys  Asn  Gly  Thr  Pro  Glu  Gly  Pro  Leu  Arg  Arg  Asn  Pro  Gly  Asn  His
     290                      295                      300

Asp  Lys  Ser  Arg  Thr  Pro  Arg  Leu  Pro  Ser  Ser  Ala  Asp  Val  Glu  Phe
305                      310                      315                           320

Cys  Leu  Ser  Leu  Thr  Gln  Tyr  Glu  Ser  Gly  Ser  Met  Asp  Lys  Ala  Ala
               325                      330                      335

Asn  Phe  Ser  Phe  Arg  Asn  Thr  Leu  Glu  Gly  Phe  Ala  Ser  Pro  Leu  Thr
               340                      345                      350

Gly  Ile  Ala  Asp  Ala  Ser  Gln  Ser  Ser  Met  His  Asn  Ala  Leu  His  Ile
          355                      360                      365

Tyr  Met  Asn  Gly  Thr  Asn  Ser  Gln  Val  Gln  Gly  Ser  Ala  Asn  Asp  Pro
     370                      375                      380

Ile  Phe  Leu  Leu  His  His  Ala  Phe  Val  Asp  Ser  Ile  Phe  Glu  Gln  Trp
385                      390                      395                           400

Leu  Arg  Arg  His  Arg  Pro  Leu  Gln  Glu  Val  Tyr  Pro  Glu  Ala  Asn  Ala
               405                      410                      415

Pro  Ile  Gly  His  Asn  Arg  Glu  Ser  Tyr  Met  Val  Pro  Phe  Ile  Pro  Leu
               420                      425                      430

Tyr  Arg  Asn  Gly  Asp  Phe  Phe  Ile  Ser  Ser  Lys  Asp  Leu  Gly  Tyr  Asp
          435                      440                      445

Tyr  Ser  Tyr  Leu  Gln  Asp  Ser  Asp  Pro  Asp  Ser  Phe  Gln  Asp  Tyr  Ile
     450                      455                      460

Lys  Ser  Tyr  Leu  Glu  Gln  Ala  Ser  Arg  Ile  Trp  Ser  Trp  Leu  Leu  Gly
465                      470                      475                           480

Ala  Ala  Met  Val  Gly  Ala  Val  Leu  Thr  Ala  Leu  Leu  Ala  Gly  Leu  Val
               485                      490                      495

Ser  Leu  Leu  Cys  Arg  His  Lys  Arg  Lys  Gln  Leu  Pro  Glu  Glu  Lys  Gln
               500                      505                      510

Pro  Leu  Leu  Met  Glu  Lys  Glu  Asp  Tyr  His  Ser  Leu  Tyr  Gln  Ser  His
          515                      520                      525

Leu
```

( 2 ) INFORMATION FOR SEQ ID NO:9:

( i ) SEQUENCE CHARACTERISTICS:
        ( A ) LENGTH: 521 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

```
Met Ser Ala Pro Lys Leu Leu Ser Leu Gly Cys Ile Phe Phe Pro Leu
 1               5                  10                 15
Leu Leu Phe Gln Gln Ala Arg Ala Gln Phe Phe Arg Gln Cys Ala Thr
            20                  25                 30
Val Glu Ala Leu Arg Ser Gly Met Cys Cys Pro Asp Leu Ser Pro Val
        35                  40                 45
Ser Gly Pro Gly Thr Asp Arg Cys Gly Ser Ser Gly Arg Gly Arg
    50                  55              60
Cys Glu Ala Val Thr Ala Asp Ser Arg Pro His Ser Pro Gln Thr Pro
 65              70                  75                 80
His Asp Gly Arg Arg Arg Arg Glu Val Trp Pro Leu Arg Phe Phe Asn
             85                  90                 95
Arg Thr Cys His Cys Asn Gly Asn Phe Ser Gly His Asn Cys Gly Tyr
            100                 105                110
Cys Arg Pro Gly Tyr Arg Gly Ala Ala Cys Asp Glu Arg Val Leu Ile
        115                 120                125
Val Arg Arg Asn Leu Leu Asp Leu Ser Lys Glu Glu Lys Asn His Phe
    130                 135                140
Val Arg Ala Leu Asp Met Ala Leu Arg Thr Thr His Pro Leu Phe Val
145                 150                 155                160
Ile Ala Thr Arg Arg Ser Glu Glu Ile Leu Gly Pro Asp Gly Asn Tyr
                165                 170                175
Pro Gln Phe Glu Asn Ile Ser Ile Thr Asn Thr Phe Val Trp Thr His
            180                 185                190
Tyr Tyr Ser Val Lys Lys Thr Phe Leu Gly Val Gly Gln Glu Ser Phe
        195                 200                205
Gly Glu Val Asp Phe Ser His Glu Gly Pro Ala Phe Leu Thr Trp His
    210                 215                220
Arg Tyr His Leu Leu Arg Leu Glu Lys Asp Met Gln Glu Met Leu Gln
225                 230                 235                240
Glu Pro Ser Phe Ser Leu Pro Tyr Trp Asn Phe Ala Thr Gly Lys Asn
                245                 250                255
Val Cys Asp Ile Cys Thr Asp Asp Leu Met Gly Ser Arg Ser Asn Phe
            260                 265                270
Asp Ser Thr Leu Ile Ser Pro Asn Ser Val Phe Ser Gln Trp Arg Val
        275                 280                285
Val Cys Asp Ser Leu Glu Asp Tyr Asp Thr Leu Gly Thr Leu Cys Asn
    290                 295                300
Ser Thr Glu Asp Gly Pro Ile Arg Arg Asn Pro Ala Gly Asn Val Ala
305                 310                 315                320
Arg Pro Met Val Gln Arg Leu Pro Glu Pro Gln Ala Val Val Gln Cys
                325                 330                335
Leu Glu Val Gly Leu Phe Asp Thr Pro Pro Phe Thr Ser Asn Ser Thr
            340                 345                350
```

-continued

| | | | | | | | | | | | | | | |
|---|---|---|---|---|---|---|---|---|---|---|---|---|---|---|
| Asn | Ser | Phe 355 | Arg | Asn | Thr | Val | Glu 360 | Gly | Thr | Ser | Asp | Pro 365 | Thr | Gly | Leu |
| Tyr | Asp 370 | Pro | Ala | Val | Arg | Ser 375 | Leu | His | Asn | Leu | Ala 380 | His | Leu | Phe | Leu |
| Asn 385 | Gly | Thr | Gly | Gly | Asn 390 | Thr | His | Leu | Ser | Pro 395 | Asn | Asp | Pro | Ile | Pro 400 |
| Val | Leu | Leu | His | Thr 405 | Phe | Thr | Asp | Ala | Val 410 | Phe | Asp | Glu | Trp | Leu 415 | Arg |
| Arg | Tyr | Asn | Ala 420 | Asp | Ile | Ser | Thr | Phe 425 | Pro | Leu | Glu | Asn | Ala 430 | Pro | Ile |
| Gly | His | Asn 435 | Arg | Gln | Tyr | Asn | Met 440 | Val | Pro | Phe | Trp | Pro 445 | Pro | Val | Thr |
| Asn | Thr 450 | Gln | Met | Phe | Val | Thr 455 | Ala | Pro | Asp | Asn | Leu 460 | Gly | Tyr | Thr | Tyr |
| Glu 465 | Ile | Gln | Trp | Pro | Ser 470 | Arg | Glu | Phe | Ser | Val 475 | Pro | Glu | Ile | Ile | Ala 480 |
| Ile | Ala | Val | Val | Gly 485 | Ala | Leu | Leu | Leu | Val 490 | Ala | Leu | Ile | Phe | Gly 495 | Thr |
| Ala | Ser | Tyr | Leu 500 | Ile | Arg | Ala | Arg | Arg 505 | Ser | Met | Asp | Glu | Ala 510 | Asn | Gln |
| Pro | Leu | Leu 515 | Thr | Asp | Gln | Tyr | Gln 520 | Cys | | | | | | | |